United States Patent [19]
Lauritzen

[11] Patent Number: 4,530,353
[45] Date of Patent: Jul. 23, 1985

[54] UNITARY ADHESIVE BANDAGE

[75] Inventor: Nels J. Lauritzen, Piscataway, N.J.

[73] Assignee: Johnson & Johnson Products, Inc., New Brunswick, N.J.

[21] Appl. No.: 440,900

[22] Filed: Nov. 12, 1982

[51] Int. Cl.³ .............................................. A61L 15/00
[52] U.S. Cl. ................................................... 128/156
[58] Field of Search .................. 604/358, 365–383; 128/155, 156; 206/438–442; 428/243, 245–249, 260–262, 274, 283–290; 156/60, 72, 73.2, 93, 196–204, 212

[56] References Cited

U.S. PATENT DOCUMENTS

| | | | |
|---|---|---|---|
| 3,030,956 | 4/1962 | Nichols | 604/358 |
| 3,900,027 | 8/1975 | Keedwell | 128/268 |
| 4,203,435 | 5/1980 | Krull et al. | 128/156 |

Primary Examiner—John D. Yasko
Assistant Examiner—Christa K. Scott
Attorney, Agent, or Firm—Wayne R. Eberhardt

[57] ABSTRACT

Adhesive bandages comprising a pad area and adjacent adhesive-coated areas are prepared from a single sheet of heat-fusible bandage material, preferably a nonwoven batt material, by overlapping the center portion of the material in a Z-fold to form a triple thickness pad area, and heat calendaring the material adjacent the desired pad area to provide a surface suitable for coating with adhesive. The integrity of the pad is preserved by heat fusing the material along the folded edges of the pad.

6 Claims, 10 Drawing Figures

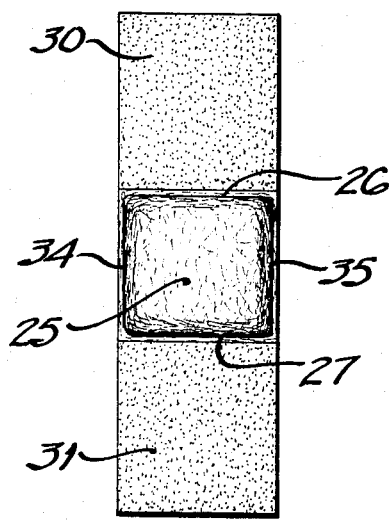
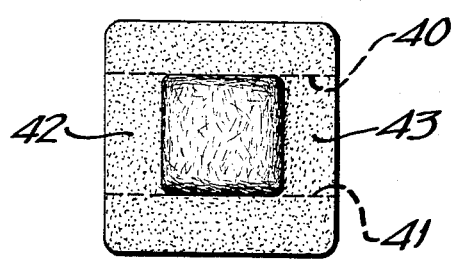
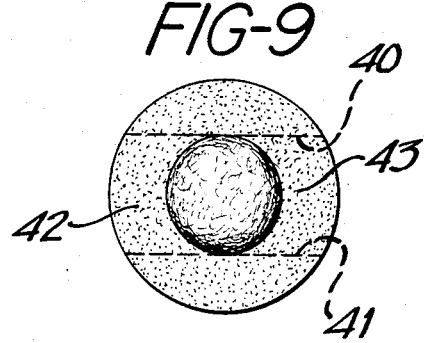
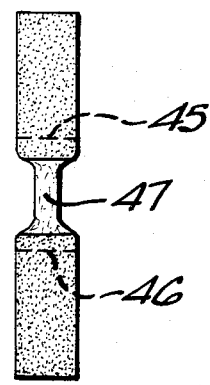

4,530,353

UNITARY ADHESIVE BANDAGE

FIELD OF INVENTION

The present invention relates to adhesive bandages comprising a central pad area and adjacent adhesive areas, and more particularly, to adhesive bandages constructed as a unit from a single piece of bandage material.

BACKGROUND OF THE INVENTION

Adhesive bandages comprising a central pad area and adjacent adhesive areas are well-known in the art and popular as first aid wound dressings. Current bandages generally comprise an elongated strip of cloth or plastic backing material coated on one surface with a pressure sensitive adhesive. A gauze or sponge pad is secured to the adhesive surface in a central location to serve as the wound cover. The wound facing surface of the pad may be plastic-coated or otherwise treated to prevent the pad from adhering to the wound. Plastic-coated release strips are placed over the adhesive areas and the entire assembly is placed in a sealed package and sterilized to be ready for use.

An alternate form of adhesive bandage, generally referred to as an island bandage, comprises a generally square, round or oval adhesive coated backing material with a centrally located pad forming an island surrounded by the adhesive surface. The adhesive surface is similarly covered by release paper before the bandage is packaged and sterilized.

The adhesive bandages of the prior art are characterized by their construction of two basic components—the adhesive coated backing material and the wound covering pad material. While such bandages are effective and desirable products, the component materials used in their construction and assembly of those component materials during production results in increased manufacturing and inventory costs.

It is accordingly an object of the present invention to provide an improved adhesive bandage. It is a further object of this invention to provide a low cost adhesive bandage through the use of inexpensive materials and low cost manufacturing techniques.

A yet further object of the present invention is to provide low cost wound dressings of the strip and island-type adhesive bandages. These and other objects of the present invention will be apparent from the ensuing description and claims of the invention.

SUMMARY

Adhesive bandages comprising an elongated strip of material having a centrally located pad area and adjacent adhesive portions extending from each side of the pad area are prepared from a single length of bandage material by overlapping the center portion of the material in a Z-fold to provide a pad area comprising a triple thickness of the bandage material. The single thickness portions of the bandage material extending from each end of the folded pad portion are permanently compacted to provide a surface suitable for coating with adhesive. The folded portion of the pad is permanently secured to the adhesive portions to prevent unfolding. The bandage is preferably constructed of a heat-bondable, absorbent, nonwoven batt material to provide loft and absorbency in the pad area, with the single thickness portions heat calendared to provide a dense, sheet-like material to accept the adhesive coating.

The bandages are conveniently prepared from a continuous web having a width equal to the overall length of the desired bandage plus twice the pad length to allow for the Z-fold construction. The continuous web is fed through a folding station which places the Z-fold down the center of the web. The folded web next passes through a hot-roll calendaring station where the edges of the folded area and the single thickness of web extending from each side of the folded area are compacted and heat-set to secure the fold and form a dense, nonwoven sheet-like structure extending from the folded area.

The web is next passed through an adhesive application station where a pressure-sensitive adhesive, preferably of a hot-melt-type, is coated onto the compacted web surfaces on either side of the folded area. Plastic-coated release paper is applied over the adhesive and the composite structure fed to a cutting station where strips are cut or stamped transverse to the machine direction of the web to obtain an adhesive bandage which is ready to be packaged and sterilized.

Additional processing steps are optionally included before cutting such as coating or glazing the wound contacting surface of the folded area to impart nonsticking properties. Also, as the bandages are cut from the composite web, the edges of the folded area may be heat-sealed or compacted along a narrow band to form a well-defined pad area.

In a similar manner, island dressings comprising a pad area surrounded by an adhesive area may be prepared by compacting the folded portion of the web in defined spaces across the width of the web. Adhesive is applied to these transverse areas as well as the longitudinal edges of the web, and the bandages are cut from the web with a central pad area surrounded by the adhesive coated material.

The Z-fold construction of the pad portion further permits wound treating agents such as antibacterial or anesthetic agents to be incorporated within the folds of the pad if desired.

The web material is preferably a nonwoven fabric composed of absorbent fibers such as cellulose or rayon and heat-fusible fibers such as polyethylene or polypropylene, in relative proportions such that the pad of the finished bandage is soft and absorbent while the heat bonded and compacted areas are strong and stable.

DESCRIPTION OF DRAWINGS

FIG. 7 is a top plan view from the pad side of a strip adhesive bandage produced by the method of the present invention with the adhesive release strips removed.

FIG. 8 is a top plan view of a square island adhesive bandage.

FIG. 9 is a top plan view of a circular island adhesive bandage.

FIG. 10 is a top plan view of a butterfly adhesive bandage.

DETAILED DESCRIPTION OF THE INVENTION

Figure 1:
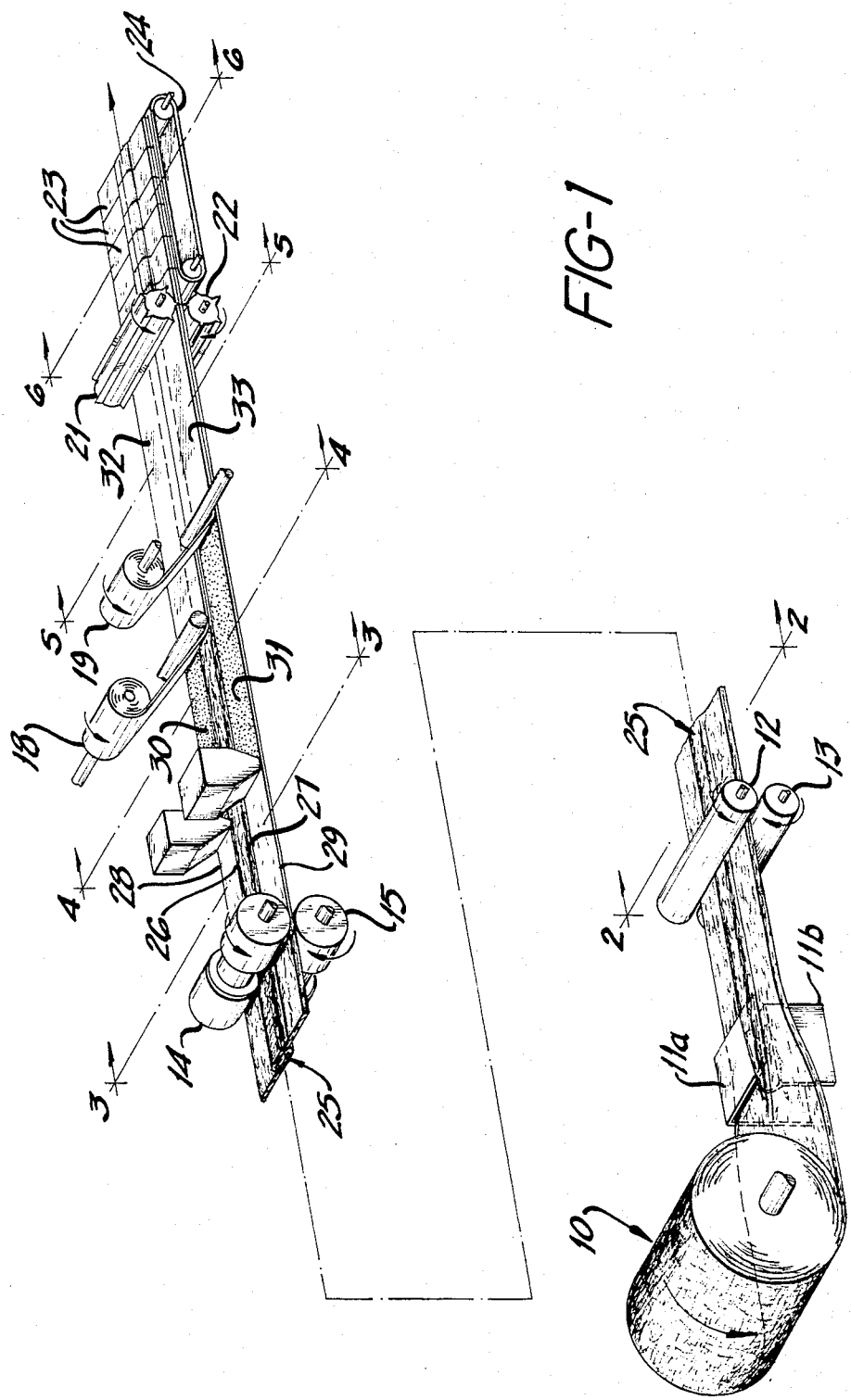
FIG. 1 is a schematic representation in perspective of a process used to produce the adhesive bandages of the present invention.

The strip adhesive bandages of the present invention having a unitized construction are fabricated from a single, continuous length of bandage material which is preferably a bulky, heat-fusible, absorbent, nonwoven fabric. The bandage is fabricated by forming a Z-fold down the center of the fabric, securing the Z-fold by heat sealing the edges thereof, and heat fusing the edge widths of the fabric extending from the folded portion to provide surfaces capable of accepting an adhesive. After applying the adhesive and covering the adhesive surfaces with release papers, the web is cut transversely in strips the width of the desired bandage.

The central pad portion of the bandage comprises a triple thickness of the starting bandage material. Since it is generally desirable for the bandage pad to be absorbent as well as providing a cushioning effect, it is important for the initial bandage material to also possess these properties. In addition, since the Z-fold forming the pad area must be secured in some manner, the bandage material is preferably a heat-fusible composition which permits the Z-fold to be continuously and permanently heat sealed along the edges.

A bandage material meeting all the above requirements is a nonwoven fabric comprising a mixture of cellulose or other absorbent fibers and polyethylene or other heat-fusible fibers. The heat-fusible fibers are interspersed throughout the web and are preferably present in an amount of at least 10% by weight. The fabric preferably has sufficient thickness or bulk so that the triple-layered pad has a thickness of at least 2 mm in the final bandage. Nonwoven webs useful in the practice of the present invention are known in the art for use in other applications. See, for example, U.S. Pat. Nos. 2,774,128; 3,067,747; 4,083,913; 4,160,159; and 4,307,721.

A particularly preferred bandage material is a low density, highly absorbent, thermal bonded nonwoven fabric comprising absorbent fibers and staple length polyester/polyethylene conjugate fibers. These nonwoven fabrics are produced by a process which includes producing a web comprising absorbent fibers and staple length polyester/polyethylene conjugate fibers; subjecting the web to a temperature sufficient to fuse the lower melting component of the conjugate fibers without fusing the higher melting component while maintaining the web under little or no compression; and cooling the web to resolidify the lower melting component of the conjugage fibers, thereby forming a nonwoven fabric bonded at sites where the conjugate fibers touch each other and adjacent absorbent fibers.

A particularly preferred nonwoven fabric is a laminate comprising a core of a mixture of short-length natural cellulose fibers and staple length polyester/polyethylene conjugate fibers, and a light weight veneer of heat-fusible fibers on each surface of the core. The composite web is passed through a through-air heater to fuse the lower melting component of the conjugate fibers while maintaining the fibrous integrity of these fibers, and to fuse or soften the surfaces of the heat-fusible fibers in the two outer veneers. As the material emerges from the heater and cools, the fused surfaces of the lower melting component of the conjugate fibers, i.e., the polyethylene, solidify, and bonds form where these surfaces touch each other and other fibers.

The thermal-bonded, nonwoven fabrics particularly useful in the practice of the present invention employ polyester/polyethylene conjugate fibers wherein at least about 50 percent of the surface of the individual fibers is polyethylene. Most preferred are sheath/core fibers with the polyethylene as the sheath and the polyester as the core. The fibers will usually have a denier within the range of from about 1 to about 6, and a length within the range of from about ½ inch to about 3 or 4 inches.

Absorbent fibers employed in such thermal-bonded, nonwoven fabrics include rayon staple fibers, cotton fibers, short length natural cellulose fibers such as wood pulp fibers and cotton linters, and mixtures thereof.

Heat-fusible fibers used in the veneer of the nonwoven fabric are preferably staple length conjugate fibers. However, if desired, other types of heat-fusible fibers such as polypropylene homofil fibers can be used in the veneer. The veneer can also contain other fibers, such as rayon, cotton, or polyester staple fibers.

The above bonded, nonwoven fabrics normally have basis weights from about ¼ to about 6 ounces per square yard. The bulk density of the fabrics is usually below about 0.15 gram per cubic centimeter, preferably below about 0.09 gram per cubic centimeter, e.g., from about 0.02 to about 0.09 gram per cubic centimeter, and more preferably, from about 0.025 to about 0.06 gram per cubic centimeter. The fabrics preferably have an absorbent capacity, as measured by a Gravimetric Absorbency Tester, of at least 600 percent and preferably at least 1400 percent, exclusive of any nonabsorbent layer such as a veneer of 100 percent fusible fibers.

Figure 2:
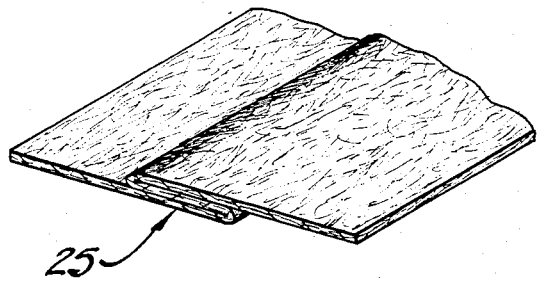
FIG. 2 is a cross-sectional view in perspective of the folded web through line 2—2 of FIG. 1.
Figure 3:
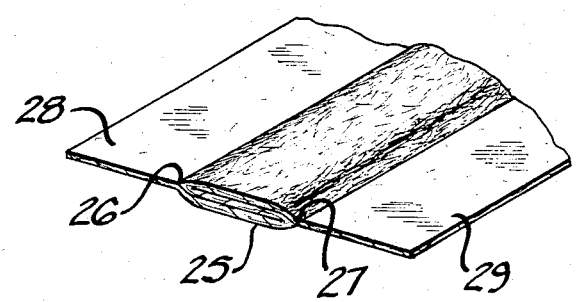
FIG. 3 is a cross-sectional view in perspective of the folded web after compaction, through line 3—3 of FIG. 1.

The process of preparing adhesive strip bandages from a continuous roll of bonded, nonwoven fabric bandage material will be better understood by reference to FIGS. 1 through 8. In FIG. 1, the center portion of nonwoven fabric from roll 10 is lapped into a Z-fold by plows 11a and 11b and passes through nip rolls 12 and 13. The cross section of the fabric leaving the nip rolls with Z-fold 25 running down the length of the fabric is illustrated in FIG. 2. The folded fabric next passes between hot calendaring rolls 14 and 15 where the edges 26 and 27 of the Z-folded portion are secured and the side widths 28 and 29 of fabric extending from the folded portion are compacted under pressure to form a thin, dense, sheet-like material. Roll 14 includes a bridging center section to avoid compacting the folded area of the fabric. The cross section of the resulting compacted product is illustrated in FIG. 3.

Figure 4:
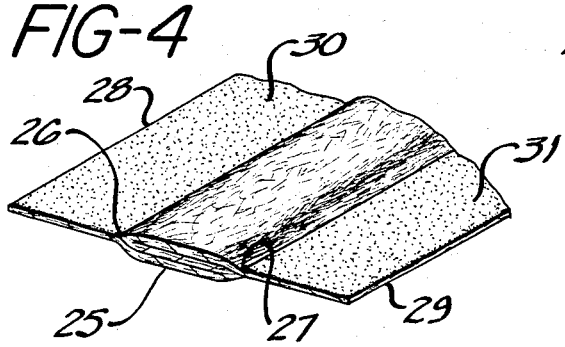
FIG. 4 is a cross-sectional view in perspective of the compacted web after application of adhesive, through line 4—4 of FIG. 1.

The compacted material next passes through the adhesive application station where a pressure-sensitive, skin-compatible adhesive is applied from reservoirs 16 and 17 to the compacted side portions of the material, the adhesive coating being designated as 30 and 31. FIG. 4 is a view in cross section of the adhesive-coated material. The adhesive may be any pressure-sensitive, medical grade adhesive suitable for use in adhesive bandages, and is preferably a hypoallergenic hot melt adhesive. Emulsion adhesives may also be used provided the adhesive application station includes means for drying the adhesive after application.

Figure 5:
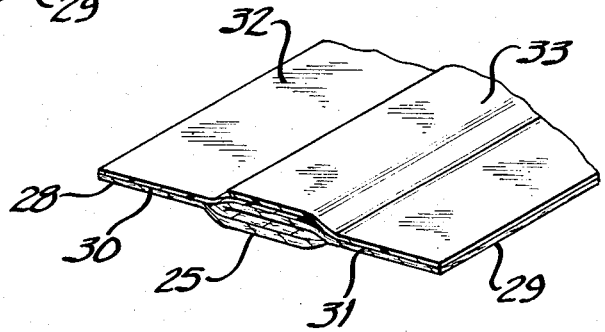
FIG. 5 is a cross-sectional view in perspective of the web of FIG. 4 after application of adhesive release papers, through line 5—5 of FIG. 1.
Figure 6:
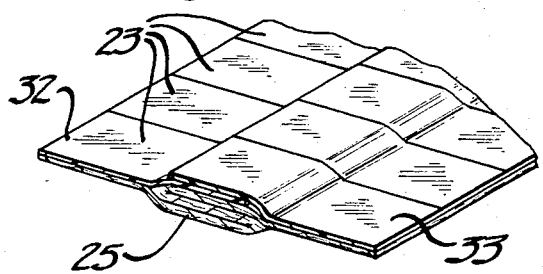
FIG. 6 is a cross-sectional view in perspective of the web of FIG. 5 after cutting into strips, through line 6—6 of FIG. 1.

As the adhesive-coated material continues through the process, the adhesive coating and the central folded area are covered by release papers 32 and 33 fed from rolls 18 and 19 respectively. The release papers preferably overlap along the center of the web over the folded area. FIG. 5 is a view in cross section of the composite material after application of the release papers.

The composite material next passes through a cutting station where cutters 21 and 22 cut the material into transverse strips 23 to obtain the strip adhesive bandages. The cut strips are carried on conveyor belt 24 to a packaging station (not shown) where individual strips are packaged in sealed envelopes prior to sterilization. The cut strips 23 are further illustrated in cross section in FIG. 6.

An individual strip bandage produced according to the present invention is illustrated in FIG. 7 with the adhesive release papers removed. In the illustrated bandage, pad 25 is set in from the longitudinal edges of the bandage by areas 34 and 35 to form a well-defined pad portion. Areas 34 and 35 are produced by compacting and heat fusing the areas on either side of the pad when the bandage strips are cut from the composite material as heretofore described.

Additional bandage configurations other than the strip bandage which may be prepared utilizing the inventive concepts of the present invention include the square island bandage of FIG. 8, and the circular island bandage of FIG. 9. In each case, the bandage is prepared from a continuous length of nonwoven fabric which has been lapped in a Z-fold over the central area to provide a pad of triple layer thickness. Material extending from the folded edges of the pad is heat fused to form a dense, sheet-like material. Additionally, the folded area itself is heat fused over the area which is not to form part of the bandage pad. This is conveniently accomplished by passing the folded web through an embossing roll imprinted with the desired bandage configuration. In FIGS. 8 and 9, the original edges of the Z-fold are indicated at 40 and 41 and the heat fused areas of the Z-fold are indicated at 42 and 43.

The adhesive is preferably applied to the bandages of FIGS. 8 and 9 by transfer coating after which the adhesive covering release papers may be applied. The bandages are thereafter obtained from the composite material by die cutting according to the desired bandage configuration.

Another variation of a bandage made in accordance with the present invention is the butterfly bandage of FIG. 10. In this bandage, the entire web including the central folded portion is heat calendared to form a dense, sheet-like material. The triple-ply center section has increased strength as desirable for this type of bandage. In FIG. 10, the original edges of the central Z-fold are indicated 45 and 46. A suitable adhesive is applied to the entire bandage except for the center portion indicated generally as 47. The butterfly bandage is die cut from a continuous length of material after the adhesive and covering release papers have been applied as described above.

Other bandage configurations and constructions utilizing the inventive concepts of the present invention will be apparent to those skilled in the art, the principle feature of the present invention being the total construction of an adhesive bandage or pad utilizing only one component or raw material, preferably a continuous web comprising heat-fusible fibers. Bandage flexibility and bias characteristics can be modified by altering fiber type and orientation.

The bandage material can be further modified by incorporating fiber finishes to vary absorbency characteristics or by incorporating medicaments such as bacteriocides and antibiotics. The surface of the pad intended for placement against the wound may be heat glazed or otherwise surface modified to provide wound release characteristics without significantly affecting the bulk or absorbency of the pad.

We claim:

1. An adhesive strip bandage constructed of a single piece of bulky, heat-fusible nonwoven fibrous material, said bandage having a central pad portion and adhesive-coated end portions extending outward therefrom, said pad portion comprising a triple thickness of said fibrous material formed by a Z-fold over the area of said pad portion, said adhesive coated end portions comprising a single thickness of said fibrous material heat fused into a thin sheet-like structure, said folded pad portion being secured to said adhesive-coated end portions by heat fusing along at least the folded edges thereof whereby said pad portion is secured in said folded configuration.

2. A bandage of claim 1 wherein said nonwoven fibrous material comprises a mixture of absorbent fibers with at least 10% heat-fusible fibers.

3. A bandage of claim 2 wherein said heat-fusible fibers are staple length polyester core/polyethylene sheath conjugate fibers.

4. A bandage of claim 1 wherein said nonwoven fibrous material comprises a core of a mixture of absorbent fibers and heat-fusible polyester/polyethylene conjugate fibers, and an outer veneer on both faces of said core comprising a nonwoven web of heat-fusible polyester/polyethylene conjugate fibers.

5. A bandage of claim 4 wherein said absorbent fibers are selected from the group consisting of rayon, cotton, wood pulp, cotton linters, and mixtures thereof.

6. A bandage of claim 4 wherein the surface of said pad comprising a veneer of said heat-fusible fibers is heat glazed to impart nonsticking, wound release properties to said pad.

* * * * *